(12) United States Patent  
Silver et al.

(10) Patent No.: US 7,455,408 B2  
(45) Date of Patent: Nov. 25, 2008

(54) METHOD AND APPARATUS FOR REDUCING VISUAL ABERRATIONS

(75) Inventors: David M. Silver, Bethesda, MD (US); Adrienne Csutak, Debrecen (HU)

(73) Assignee: The Johns Hopkins University, Baltimore, MD (US)

( * ) Notice: Subject to any disclaimer, the term of this patent is extended or adjusted under 35 U.S.C. 154(b) by 372 days.

(21) Appl. No.: 11/497,063

(22) Filed: Aug. 1, 2006

(65) Prior Publication Data

US 2007/0025118 A1 Feb. 1, 2007

Related U.S. Application Data

(60) Provisional application No. 60/704,402, filed on Aug. 1, 2005.

(51) Int. Cl.
 *A61B 3/00* (2006.01)
 *A61B 3/10* (2006.01)
(52) U.S. Cl. ...................... 351/246; 351/221

(58) Field of Classification Search ............... 351/200, 351/202, 221, 246, 44, 158
See application file for complete search history.

(56) References Cited

U.S. PATENT DOCUMENTS

| 5,900,923 | A * | 5/1999 | Prendergast et al. ........ 351/221 |
| 6,199,985 | B1 * | 3/2001 | Anderson .................. 351/221 |
| 6,291,498 | B1 | 9/2001 | Horn |
| 6,626,537 | B1 | 9/2003 | Odom et al. |
| 6,715,878 | B1 | 4/2004 | Gobbi et al. |
| 7,048,379 | B2 * | 5/2006 | Miller et al. ............... 351/213 |
| 2006/0285314 | A1 * | 12/2006 | Barker ..................... 362/103 |

* cited by examiner

Primary Examiner—William C Choi  
Assistant Examiner—Jack Dinh  
(74) Attorney, Agent, or Firm—Francis A. Cooch

(57) ABSTRACT

A light source is situated on a headgear device and placed to direct light toward the pupil of the eye at an intensity that causes the iris to constrict, resulting in a smaller pupil. This prevents the light scattering due to ophthalmic surgery or eye injury from entering the eye, thereby reducing or eliminating visual aberrations.

18 Claims, 5 Drawing Sheets

Temporal light source
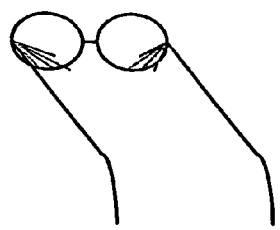
FIG. 4A
Nasal light source
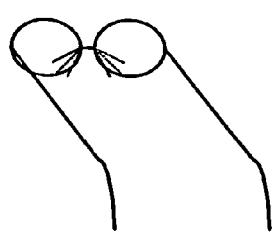
FIG. 4B
Eye-glass-like frame
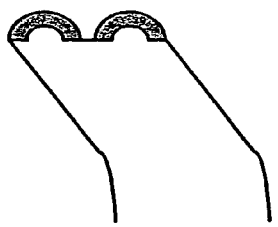
FIG. 4C
Fiber optic model
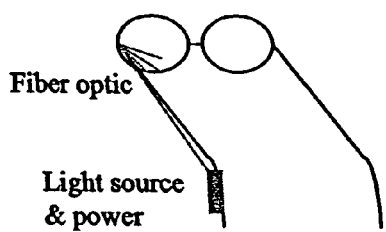
FIG. 4D
Circular light source
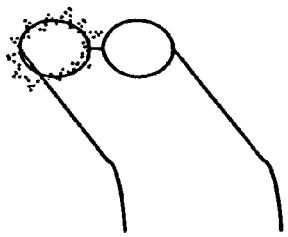
FIG. 4E
Prototype model
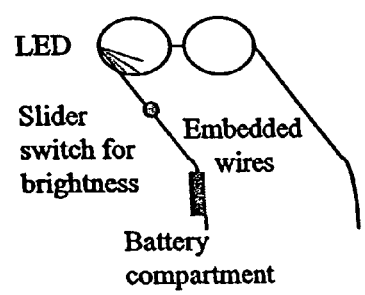
FIG. 4F
FIG. 4

METHOD AND APPARATUS FOR REDUCING VISUAL ABERRATIONS

CROSS-REFERENCE TO RELATED APPLICATIONS

This application claims the benefit of prior filed U.S. application No. 60/704,402, filed on Aug. 1, 2005, the content of which is incorporated fully herein by reference.

BACKGROUND OF THE INVENTION

1. Field of the Invention

This invention relates to a method and apparatus for correcting visual aberrations resulting from ophthalmic surgery or eye injury.

2. Description of the Related Art

Visual aberrations are sometimes found as complications following ophthalmic surgery or eye injury. For instance, with respect to laser vision correction surgery, halos, glare, starbursts and night vision difficulties are often found after laser in situ keratomileusis (LASIK). As shown schematically in FIG. 1, the aberrations are caused by light scattering that is thought to be localized in the vicinity of the outer circle of the corneal flap (flap margin) produced with a microkeratome as part of the LASIK procedure.

A retrospective case-control study of LASIK patients reported visual aberrations from a sample of 841 respondents: 30% of patients experienced halos, 27% experienced glare, and 25% experienced starbursts. [Bailey M D, Mitchell G L, Dhaliwal D K, Boxer-Wachler B S, Zadnik K. Patient satisfaction and visual symptoms after laser in situ keratomileusis. *Opthalmology* 2003; 110:1271-1378.]

Other ophthalmic surgeries in addition to LASIK that manifest similar complications include radial keratectomy (RK), photorefractive keratectomy (PRK), and laser assisted subepithelial keratectomy (LASEK). Injury to the mid-periphery of the cornea can also cause similar visual aberrations due to scar formation or other corneal wound healing abnormalities.

When visual aberrations are present, they are disturbing at best and debilitating in the extreme. The visual disability from these aberrations is particularly noticeable in dim light and night-time circumstances. For some individuals, night driving is difficult or impossible. A description of these disabilities and post-opthalmic surgery visual aberrations can be found on the websites www.visionsimulations.com and www.surgicaleyes.org.

Previously proposed solutions to reduce glare include medication (U.S. Pat. No. 6,291,498 to Horn); optical filters (U.S. Pat. No. 6,056,397 to Berlad and U.S. Pat. No. 5,930,047 to Grunz et al.); lenses (U.S. Pat. No. 6,450,636 to Ylipelkonen, et al., U.S. Pat. No. 5,428,409 to Silverstein, and U.S. Pat. No. 5,252,997 to Christenbery); polarizing lenses (U.S. Pat. No. 6,646,801 to Sley and U.S. Pat. No. 6,424,448 to Levy); and optical apertures and shields (U.S. Pat. No. 6,386,702 to Maloncon and U.S. Pat. No. 4,828,380 to Cherian). As noted, most of the above are general glare reduction systems not focused on solving the problems of visual aberrations caused by opthalmic surgery or injury. Furthermore, the use of medicine can be considered invasive, and the optical methods can reduce the light signal. The patent to Maloncon that is specifically for use by post-operative LASIK surgery patients is a mechanical system in which the size of the viewing aperture in the device can be changed. What is needed, therefore, is a non-invasive, simple, effective method and apparatus to reduce visual aberrations resulting from surgery or injury.

SUMMARY OF THE INVENTION

The invention solves the above problems by making use of the eye's natural response mechanism to control the amount of light that will enter the eye. Thus, light scattering caused by the corneal flap created during opthalmic surgery or scarring caused by eye injury will be reduced or eliminated resulting in reduction or elimination of visual aberrations. More specifically, to counteract the light scattering, the invention uses a light source to direct light toward the pupil of the eye at an intensity that causes the iris to constrict, resulting in a smaller pupil. The constricted pupil limits the light entering the eye to light that has passed through a smaller central circular portion of the cornea. Since the central cornea does not include the source of light scattering (flap margin area in LASIK, peripheral corneal wound or scar region), the visual aberration will be reduced or eliminated.

BRIEF DESCRIPTION OF THE DRAWINGS

FIG. 4, consisting of FIGS. 4A to 4F, illustrates six different embodiments of the invention.

DETAILED DESCRIPTION

The present invention is counter-intuitive since it uses light itself to cause a restriction in the amount of light that can enter the eye. As is known, the human pupil responds to the exposure of light with maximum constrictive sensitivity to light of ~560 nm (green-yellow); sensitivity is less in the blue and red portions of the spectrum. The diameter of the pupil is related to illumination. One measure of this relation is as follows:

$$\log d = 0.8558 - 0.000401 (\log b + 8.60)^3$$

where d is pupil diameter in mm and b is luminance in cd/m². [Davson H. Physiology of the Eye, 5$^{th}$ Ed. Pergamon Press: New York; 1990, p. 757.] The pupil responds to both blinking and steady light. Direct light reflex is the constrictive response of the pupil to light on the eye, while indirect or consensual light reflex is the constrictive response of the pupil of the unstimulated eye. Stimulation of both eyes causes greater constriction of the pupils than light stimulation of a single eye.

Figure 1:
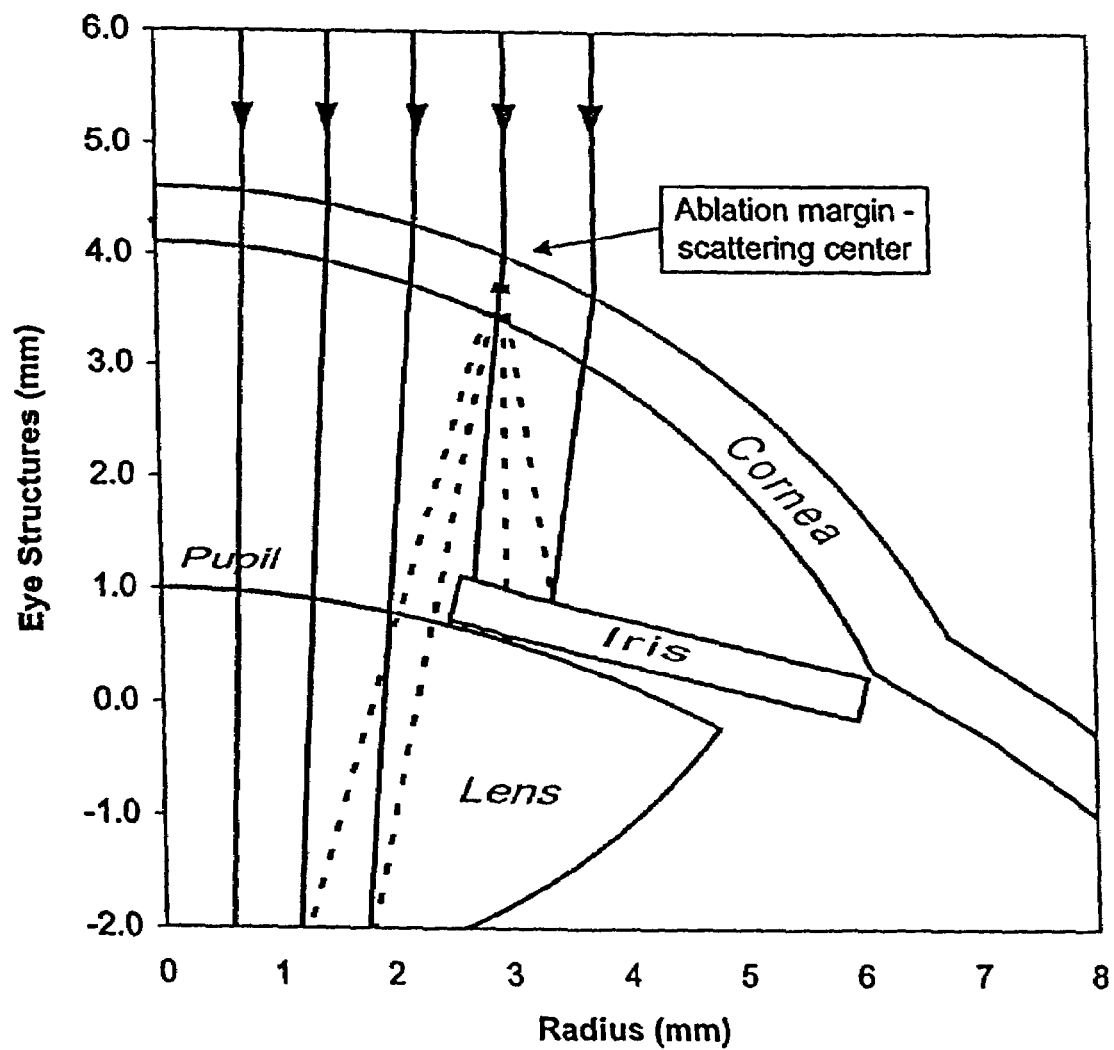
FIG. 1 is an ocular model of the eye illustrating how a visual aberration is created by light scattering localized at the margin of the corneal flap created during opthalmic surgery.
Figure 2:
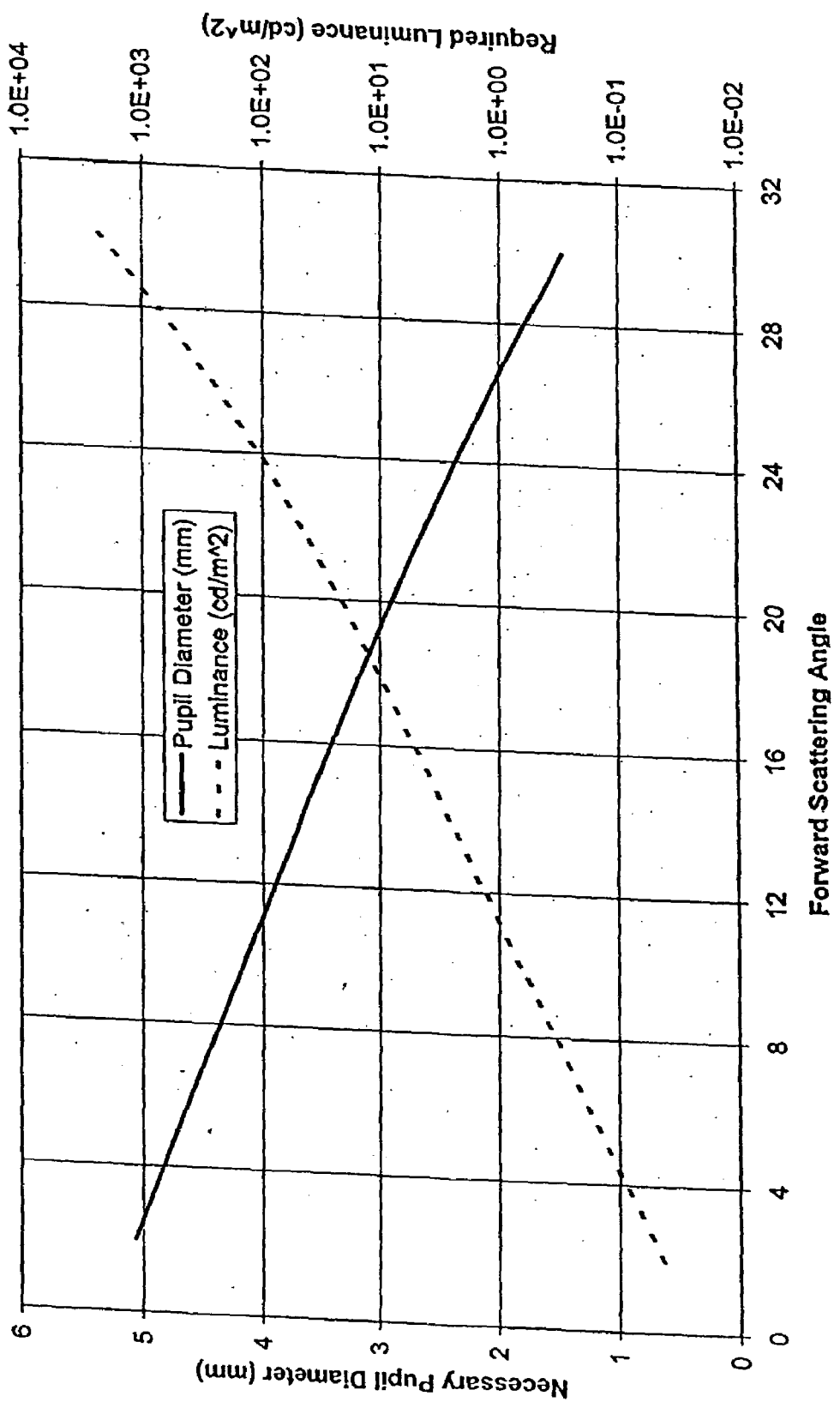
FIG. 2 is a graph illustrating pupil diameter and luminance as a function of forward scattering angle.

The invention makes use of the eye's natural response mechanism to control the amount of light that will enter the eye. This results in the elimination or reduction of light scattering caused by the corneal flap created during opthalmic surgery or scarring caused by eye injury entering the eye, thereby resulting in elimination or reduction of visual aberrations. FIG. 2 illustrates the relationship of pupil size and luminance as a function of the forward scattering angle of the light in order to reduce or eliminate visual aberrations.

Figure 3:
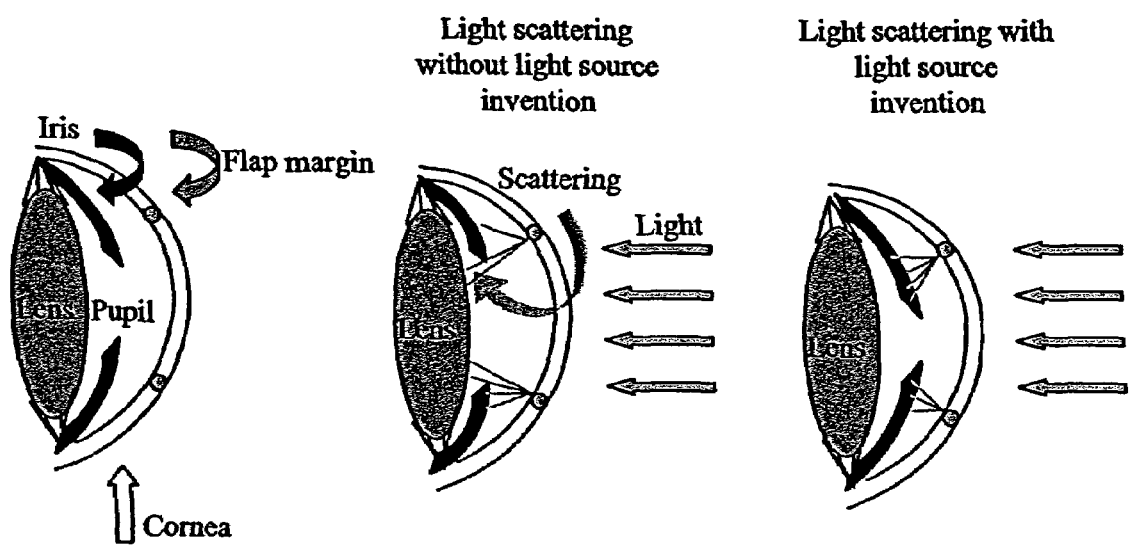
FIG. 3, consisting of FIGS. 3A, 3B, and 3C, illustrates, respectively, a post-operative eye with a corneal flap margin, light scattering at the flap margin and a constricted pupil that prevents the scattered light from entering the eye.

A post opthalmic surgery eye is shown in FIG. 3A, including the margin of the corneal flap. FIG. 3B illustrates light scattering that can be caused at the flap margin and enter the eye without the use of the invention. The invention uses a light source to direct light toward the pupil of the eye at an intensity that causes the iris to constrict, resulting in a smaller pupil. As shown in FIG. 3C, the constricted pupil limits the light entering the eye to light that has passed through a smaller central circular portion of the cornea. Since the central cornea does not include the source of light scattering (flap margin area in LASIK, peripheral corneal wound or scar region), the visual aberration will be reduced or eliminated.

In practice, as shown in FIG. 4, the invention comprises a light source situated on a headgear device to be worn by the user. As noted previously, the light is then directed toward the pupil of the eye at an intensity that causes the iris to constrict resulting in a smaller pupil and, hence, a reduction/elimination of scattered light entering the eye and causing a visual aberration. By situating the light on a headgear, for example, eyeglasses, eyeglass-like frames or goggles, the invention can be worn during any activity (sitting, walking, driving) and in any environment (especially dim and night-time lighting) and, thereby, provides aberration reduction with a solution to the need for mobility for the person suffering from visual aberrations.

As shown in FIGS. 4A through 4F, the invention can have many different embodiments, but all include a light source, which could be a light bulb, light emitting diode (LED), laser, fiber-optic (FIG. 4D), etc., either used alone or fitted with a lens (not shown). Examples of the headgear device incorporating the light source can be, as noted above, eyeglasses, goggles (not shown), or eyeglass-like frames (FIG. 4C). In some embodiments, it might be necessary or desirable to include corrective lenses in the eyeglass frames; in other embodiments, the lens could be absent or plano (a stylistic choice). The light source could be placed in a number of different locations on the headgear, for example, temporal (FIG. 4A), nasal (FIG. 4B), and circular (FIG. 4E), and the light could be directed toward one eye or toward both eyes. Any color (single or multiple wavelength) including white light could be used and the brightness could be fixed or adjustable by the individual to be just sufficiently bright to reduce or eliminate the visual aberration. The preferred intensity of light would be a compromise between the positive effect of aberration reduction and the possible negative effect of the light being a distraction or nuisance.

As shown in FIG. 4F, an embodiment of the invention comprises a miniature LED mounted in each temporal corner of an eyeglass or eyeglass-like frame and having a power source and brightness/intensity adjusting control co-located in the distal end of the temples of the frame, near or behind the ear. The power source could be a miniature battery and the control mechanism could be a miniature slider-type potentiometer.

Figure 5:
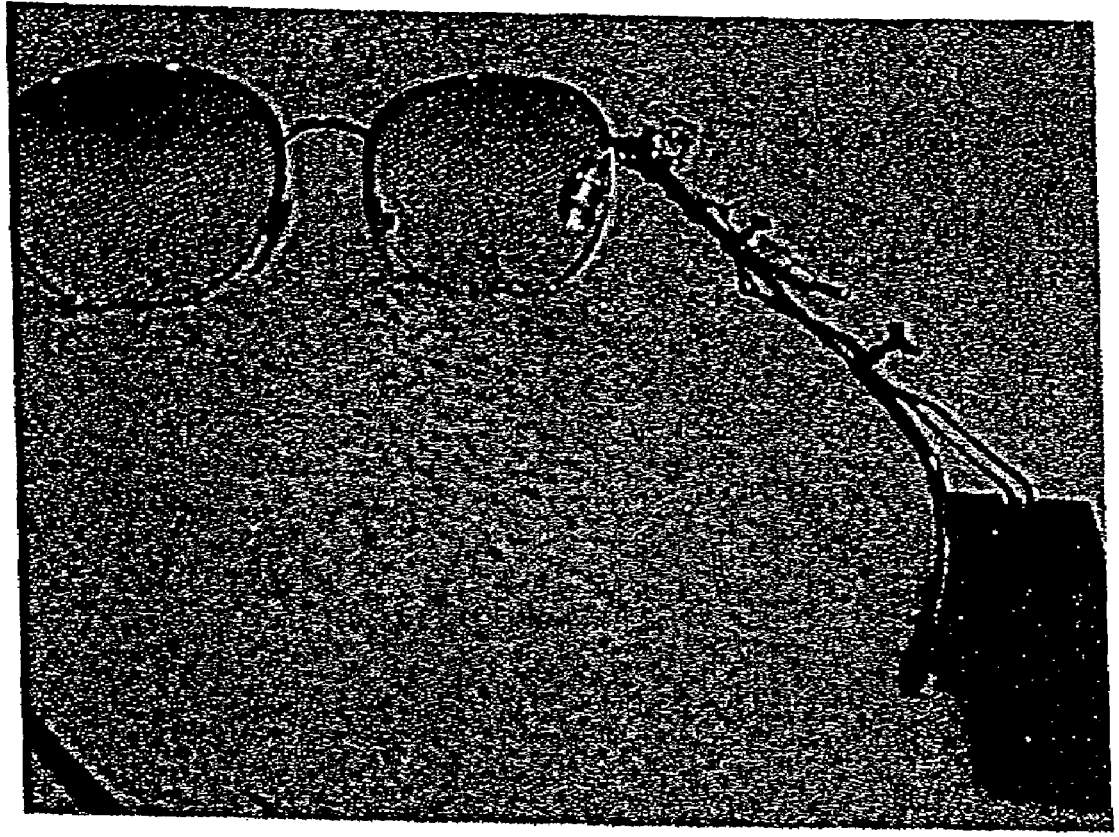
FIG. 5 illustrates an operating prototype of the invention.

An operating prototype of the invention (shown in FIG. 5) was constructed using the following: a yellow LED with peak emission at 587 nm, viewing angle of 30° (angle between half intensity points on either side of direct viewing) with a peak luminance of 1.9 mcd at a nominal 20 uA and 2.1 V; a 10 kΩ potentiometer; and a 3 V battery circuit. A mid-level brightness of the LED, located in the temporal corner of an eyeglass frame in dim light and night environments, produced a pupil constriction that could be detected by an observer. The presence of the LED was noticeable but not a disturbance to the person wearing the device.

While there has been described herein the principles of the invention, it is to be understood by those skilled in the art that this description is made only by way of example and not as a limitation to the scope of the invention. Accordingly, it is intended by the appended claims to cover all modifications of the invention which fall within the true spirit and scope of the invention.

We claim:

1. A method for reducing visual aberrations in an eye due to light scattering resulting from a corneal flap or a scar in the eye due to ophthalmic surgery or eye injury, the method comprising the steps of:
   placing a light source near the eye;
   directing light from the light source toward the eye, the intensity of the light from the light source being sufficient to cause the iris of the eye to constrict, thereby reducing the size of the pupil of the eye and preventing the scattered light from entering the eye and causing visual aberrations.

2. The method as recited in claim 1, wherein the intensity of the light directed toward the eye can be varied.

3. The method as recited in claim 2, wherein the intensity of the light is varied using a potentiometer.

4. The method as recited in claim 1, further comprising the step of providing a power source for the light source.

5. The method as recited in claim 1, wherein the light source is held near the eye by a light source holder comprising one of eyeglasses, eyeglass-like frames, and goggles.

6. The method as recited in claim 5, wherein the light source holder further comprises corrective lenses.

7. The method as recited in claim 1, wherein the light source comprises one of a light bulb, a light emitting diode, a laser and a fiber optic.

8. The method as recited in claim 7, wherein the light source is fitted with a lens.

9. The method as recited in claim 1, wherein the light source comprises any color of light.

10. An apparatus for reducing visual aberrations in an eye due to light scattering resulting from a corneal flap or a scar in the eye due to ophthalmic surgery or eye injury, the apparatus comprising:
    a light source; and
    means for holding the light source;
    whereby light from the light source is directed toward the eye, the intensity of the light being sufficient to cause the iris of the eye to constrict, thereby reducing the size of the pupil of the eye and preventing the scattered light from entering the eye and causing visual aberrations.

11. The apparatus as recited in claim 10, further comprising means for varying the intensity of the light.

12. The apparatus as recited in claim 11, the means for varying the intensity of the light comprising a potentiometer.

13. The apparatus as recited in claim 10, further comprising a power source.

14. The apparatus as recited in claim 10, the means for holding the light source comprising one of eyeglasses, eyeglass-like frames, and goggles.

15. The apparatus as recited in claim 10, the light source comprising one of a light bulb, a light emitting diode, a laser, and a fiber-optic.

16. The apparatus as recited in claim 15, wherein the light source is fitted with a lens.

17. The apparatus as recited in claim 10, the means for holding the light source further comprising corrective lenses.

18. The apparatus as recited in claim 10, the light source comprises any color of light.

* * * * *